US009161959B2

(12) United States Patent
Xu et al.

(10) Patent No.: US 9,161,959 B2
(45) Date of Patent: *Oct. 20, 2015

(54) USE OF A VEGETABLE DRUG COMPOSITION IN THE MANUFACTURING OF PHARMACEUTICAL PREPARATION FOR THE TREATMENT OF PORTAL HYPERTENSION CAUSED BY HEPATOCIRRHOSIS

(75) Inventors: Lieming Xu, Shanghai (CN); Cheng Liu, Shanghai (CN); Ping Liu, Shanghai (CN)

(73) Assignee: SHANGHAI SUNDISE CHINESE MEDICINE TECHNOLOGY DEVELOPMENT CO., LTD, Shanghai (CN)

( * ) Notice: Subject to any disclaimer, the term of this patent is extended or adjusted under 35 U.S.C. 154(b) by 263 days.

This patent is subject to a terminal disclaimer.

(21) Appl. No.: 12/451,133

(22) PCT Filed: Apr. 28, 2008

(86) PCT No.: PCT/CN2008/000864
§ 371 (c)(1),
(2), (4) Date: Oct. 27, 2009

(87) PCT Pub. No.: WO2008/134932
PCT Pub. Date: Nov. 13, 2008

(65) Prior Publication Data
US 2010/0119541 A1    May 13, 2010

(30) Foreign Application Priority Data
Apr. 29, 2007 (CN) .......................... 2007 1 0040332

(51) Int. Cl.
| A61K 36/068 | (2006.01) |
| A61K 36/537 | (2006.01) |
| A61K 36/424 | (2006.01) |
| A61K 36/79  | (2006.01) |
| A61K 36/15  | (2006.01) |
| A61K 36/53  | (2006.01) |
| A61K 36/57  | (2006.01) |
| A61K 36/73  | (2006.01) |

(52) U.S. Cl.
CPC ............. *A61K 36/424* (2013.01); *A61K 36/068* (2013.01); *A61K 36/15* (2013.01); *A61K 36/53* (2013.01); *A61K 36/57* (2013.01); *A61K 36/73* (2013.01)

(58) Field of Classification Search
None
See application file for complete search history.

(56) References Cited

U.S. PATENT DOCUMENTS

| 2007/0160626 A1* | 7/2007 | Zhang et al. ............. 424/195.15 |
| 2010/0093099 A1  | 4/2010 | Ma et al. |
| 2010/0093103 A1  | 4/2010 | Ma et al. |
| 2010/0119541 A1  | 5/2010 | Xu et al. |

FOREIGN PATENT DOCUMENTS

| CN | 1243743       | * | 2/2000 |
| CN | 99113887.2    |   | 8/2001 |
| CN | 1472532       |   | 2/2004 |
| CN | 1569104       | * | 1/2005 |
| CN | 1669573       |   | 9/2005 |
| CN | 02136002.2    |   | 9/2005 |
| CN | 1839996       |   | 10/2006 |
| CN | 1925864       |   | 3/2007 |
| CN | 2007100401416 |   | 4/2007 |
| CN | 1959409       |   | 5/2007 |
| CN | 101042380     |   | 9/2007 |
| CN | 101078712     |   | 11/2007 |
| CN | 200710040331.8|   | 12/2009 |
| CN | 200510028951.0|   | 3/2010 |
| CN | 1899415       |   | 5/2010 |
| JP | 1165583       |   | 6/1989 |
| KR | 20060038027   |   | 5/2006 |
| WO | 01/41778      |   | 6/2001 |
| WO | 2004/014409   |   | 2/2004 |
| WO | 2007/020382   |   | 2/2007 |

OTHER PUBLICATIONS

Xu et al. Effect of Relieving Blood Stasis, Strengthening Spleen and Soothing Liver Therapy in Improving Hepatic Function in Patients After Liver Carcinomectomy. Zhongguo Zhong Xi Yi Jie He Za Zhi. Oct. 21, 2001. (10) pp. 742-743. (Abstract only).*
Palmer. Doctor Melissa Palmer's guide to hepatitis and liver disease. Penguin 2004. 1 Page.*
Aube et al. Ultrasonographic diagnosis of hepatic fibrosis or cirrhosis. Journal of Hepatology. 1999. 30. 472-478.*

(Continued)

*Primary Examiner* — Chris R Tate
(74) *Attorney, Agent, or Firm* — Ascenda Law Group PC

(57) ABSTRACT

Use of a vegetable drug composition in the manufacturing of a pharmaceutical preparation for the treatment of portal hypertension caused by hepatocirrhosis, said preparation comprises 25-38% of extract of radix *Salviae Miltiorrhizae*, 20-25% of extract of herb *Gynostemmae Pentaphylli*, 1-6% of alcoholic extract of fructus *Schisandrae Chinensis*, 19-26% of extract of *Cordyceps*, 6-8% of extract of pollen Pini, 6-10% of extract of semen Persicae. Said preparation can improve hepatic cell degeneration, necrosis, intraheptic hemorrhage, fiber proliferation, and reduce pressure of portal vein in mammal. A preparation method of said preparation is disclosed.

3 Claims, 3 Drawing Sheets

(56) References Cited

OTHER PUBLICATIONS

Tan et al. Influence of *Salvia miltiorrhizae* and *Astragalus membranaceus* on hemodynamics and liver fibrosis indexes in liver cirrhotic patients with portal hypertension. Zhongguo Zhong Xi Yi Jie He Za Zhi. 2001. May; 21 (5) Abstract.*

Oneearthherbs.squarespace.com. Salvia Root. Retrieved from the Internet. <http://oneearthherbs.squarespace.com/important-herbs/salvia-root-salvia-miltiorrhiza.html>. Retrieved on Aug. 12, 2011. pp. 1-3.*

Song et al. Protection of a polysaccharide from *Salvia miltiorrhiza*, a Chinese medicial herb against immunological liver injury in mice. International Journal of Biological Macromolecules. 43 (2008). pp. 170-175.*

Dhgate Factory. Retrieved from the internet. <http://factory.dhgate.com/biochemical/cordycepin-polysaccharides-p38634026.html>.*

Dou, et al, "Analysis of Lignans in serum of rats after oral administration of compound Wurenchun capsules by UPLC-MS/MS", Chinese Traditional Patent Medicine, Apr. 2007, vol. 29(4), pp. 550-555.

Yan, et al, "Pharmacokinetics study of schisandrin in *Shengmai granule*", TraiditonalChinese Drug Research & Clinical Pharmacology, Jan. 2006, vol. 17(1), pp. 36-39.

Liao, et al, "The study in situ on rat intestinal absorption of the active components in GuizhiFuling capsule", Chin. J. Nat. Med., Sep. 2005, vol. 3(5), pp. 303-307.

Xie, et al, "Determinination of anthraquinones and amygdalin in "Taohe Chengqi Decoction", by HPLC", SH. J. TCM, Jul. 2006, vol. 40(7), pp. 73-76.

Pan, et al, "Pharmacokinetics and bioavailability study of danshensu in rat", China Journal of Chinese Materia Medica, Jan. 2008, vol. 33(2), pp. 146-149.

Chen et al, "LC-MS/MS-based measurement of danshen phenolic acids in plasma", Chin. J. Clin Pharmacol Ther, Jul. 2007, vol. 12(7), pp. 748-755.

Tan, et al, "Research Concerning Influence of "Fuzheng Huayu Decoction" on Hepatocellular Apoptosis in Rats with DMN Liver Fibrosis", A Collection of Papers of the 12th National Symposium on Liver Disease with Chinese Integrative Medicine, 2003, pp. 219-223.

She, et al, "Clinical Research of Ganping Capsule Treating Liver Fibrosis in Patients with Chronic Hepatitis B", Chinese Heptology, Dec. 2002, vol. 7(4), pp. 254-255.

Lou, et al, "Comparison of schisandrin and schisandrin B in rat serum and plasma after ig Compound Wurenchun Capsules", Chinese Traditional and Herbal Drugs, vol. 37(10), Oct. 2006; pp. 1486-1489.

Xu, et al, "Determination of schizandrin in rat plasma by high-performance liquid chromatography—mass spectrometry and its application in rate pharmacokinetic studies", Journal of Chromatography B, vol. 828, 2005, pp. 55-61.

He, et al, "Analysis of lignan constituents from *Schisandra chinensis* by liquid chromatography—electrospray mass spectrometry", Journal of Chromatography A, vol. 757, 1997, pp. 81-87.

Database Biosis (Online) Biosciences Information Service, Philadelphia, PA, Feb. 2000; Baek Nam-In, et al, "Isolation of anticonvulsant compounds from the fruits of *Schizandra chinensis* Baili" Database accession No. PREV200000198785.

Churchwell, et al, "Improving LC-MS sensitivity through increases in chromatographic performance: Comparisons of UPLC-ES/MS/MS to HPLC-ES/MS/MS", Journal of Chromatography B, vol. 825, 2005, pp. 134-143.

Park, et al, "HPLC Assay and Bioequivalence Evlaution of Biphenyl Dimethyl Dicarboxylate (DDB) Products", J. Liq. Chrom. & Rel. Technol., vol. 21(12), 1998, pp. 1833-1843.

Zhao, et al, "HPLC with Column Switching Coupled to APCI-MS for Pharmacokinetic Study of Amygdalin in Rabbit Plasma", Chromatographia, vol. 65, 2007, pp. 149-153.

Kang, et al, "Micellar electrokinetic chromatography for the analysis of D-amygdalin and its epimer in apricot kernal", Journal of Chromatography A, vol. 866, 2000, pp. 253-259.

Liu, et al, "Effect of Fuzheng Huayu formula and its actions against liver fibrosis", Chinese Medicine, vol. 4(12), 2009, pp. 1-11.

Wang, et al, "Fuzheng Huayu recipe and vitamin E reverse renal interstitial fibrosis through counteracting TGF-B1-induced epithelial-to-mesenchymal transition", Journal of Ethnopharmacology, vol. 127, 2010, pp. 631-640.

Office Action dated Feb. 12, 2010 Issued by the State Intellectual Property Office of the People's Republic of China regarding Application No. 2007100403322.

U.S. Appl. No. 12/451,148, filed Oct. 27, 2009.

European Search Report regarding EP Application No. 08748426.7, Apr. 2010.

European Search Report regarding EP Application No. 08748424.2, Apr. 2010.

Gu J et al. Effects of Fuzheng Huayu Capsule on Portal Hemodynamics in Patients with Liver Cirrhosis vol. 39, Nr:11, pp. 31-32.

Tan C. Effects of Fuzheng Huayu Decoction on Hepatocellular Apoptosis in Rats with Dmn Liver Fibrosis vol. 39, Nr:11, pp. 31-32—Abstract.

* cited by examiner

Endothelin content in hepatic tissuepg/mg )

Endothelin content in hepatic tissuepg/mg )

USE OF A VEGETABLE DRUG COMPOSITION IN THE MANUFACTURING OF PHARMACEUTICAL PREPARATION FOR THE TREATMENT OF PORTAL HYPERTENSION CAUSED BY HEPATOCIRRHOSIS

CROSS REFERENCE TO RELATED APPLICATIONS

The present application is a 35 U.S.C. §371 national stage filing of International Patent Application No. PCT/CN2008/000864, filed on Apr. 28, 2008, which claims priority to Chinese Patent Application No. 200710040332.2, filed on Apr. 29, 2007. The disclosures of International Patent Application No. PCT/CN2008/000864 and Chinese Patent Application No 200710040332.2 are incorporated herein by reference in their entireties.

TECHNICAL FIELD

This invention belongs to the application field of the strengthening body resistance and dissipating blood stasis botanical composition, particularly involves the effect of a strengthening body resistance and dissipating blood stasis botanical composition in treatment of cirrhotic portal hypertension.

BACKGROUND ART

Hepatic cirrhosis is a pathologic change of diffuse hepatic fibrosis accompanied with tuberculation. Incidence of hepatic cirrhosis in our country reaches more than 1 million cases/year (mainly associated with viral hepatitis), with 110,000 deaths annually, which not only severely endangers people's health but also brings a heavy social economic burden to our country.

Portal hypertension is the main complication of hepatic cirrhosis, and is the main factor that determining the prognosis of hepatic cirrhosis. The activation (generating a huge amount of the extracellular matrix, forming the hepatic sinusoid capillarization and fibrous septum) and contraction (narrowing the hepatic sinus) of hepatic stellate cells (HSC) are the key link in forming cirrhotic portal hypertension. Endothelin (ET) is one of the important vaso-active substances causing HSC contraction.

Portal hypertension is an inevitable consequence of hepatic cirrhosic after a certain period of development. The main clinical manifestations include splenomegaly, portacaval collateral circulation formation and ascites. Upper gastrointestinal hemorrhage is the main complication of portal hypertension, and rupture of esophageal and gastric fundus varices is the main causa morbi. In recent years, though great strides have been made in medical and surgical treatment, the prognosis is not improved significantly. Upper gastrointestinal bleeding is still the main cause of death in patients with cirrhotic portal hypertension. Within the first and second years of diagnosis with varices, the risk of hemorrhage is 25-35%, and most happen in the first year. Most studies indicate that the mortality of first bleeding is 30%-50%, of which about 60% patients die of bleeding out of control.

Actively prevent upper gastrointestinal bleeding and rebleeding has an important significance for reducing risk of bleeding, increasing survival rate and improving prognosis. Modern medicine has no effective measure to prevent bleeding of mild esophageal varices. For moderate and severe esophageal varices; beta-blocker propranolol (Inderal) is the first choice to reduce Portal venous pressure and prevent upper gastrointestinal hemorrhage. However, due to some patients have contraindications or side effects to beta-blocker, they usually can not tolerate the treatment, besides, beta-blocker has no effect on the main causes of portal hypertension, i.e. HSC contraction and hepatic fibrosis, so beta-blocker can only alleviate the symptoms rather than remove the root causes.

Formula of strengthening body resistance and dissipating blood stasis is a drug developed by our company to treat chronic hepatitis and hepatic fibrosis, consisting of *salvia miltiorrhiza*, peach kernel, *Cordyceps* Mycelium etc. Two preparations (capsule and tablet) based on this formula have obtained marketing approval from State Food and Drug Administration, with name of China Patent "A Chinese Herbal Compound Preparation for Chronic Liver Disease and the Preparation Method", application No. 200610023308.3. In which, there is no observation report on the use of strengthening body resistance and dissipating blood stasis preparation for cirrhotic portal hypertension.

CONTENTS OF THE INVENTION

The technical problem aims to be resolved by this invention is to provide a botanical composition of strengthening body resistance and dissipating blood stasis for use in the treatment of cirrhotic portal hypertension, which provides significant improvements on the degeneration of liver cells, necrosis, intrahepatic hemorrhage, and fibroplasia in rat, and markedly decreases the portal venous pressure.

Application of a botanical composition of strengthening body resistance and dissipating blood stasis in the treatment of cirrhotic portal hypertension.

The described botanical composition of strengthening body resistance and dissipating blood stasis comprises the following active ingredients:

*Salvia miltiorrhiza* extract 25-38%, *Gynostemma pentaphyllum* extract 20-25%, *Schisandra chinens* alcohol extract 1-6%, *Cordyceps* Mycelium extract 19-26%, pine pollen extract 6-8%, and peach kernel extract 6-10%, added by adjuvant.

The application of a botanical composition of strengthening body resistance and dissipating blood stasis described includes the following steps:

(1) In accordance with the formula ratio, proportionally weigh *salvia miltiorrhiza*, peach kernel, and *Gynostemma pentaphyllum*, add water and decocting, combine the filtrate, take the supernatant, and concentrate into extractum, cool down, add ethanol to achieve ethanol content of 70%, standing, filtering, take the filtrate, concentrate and dry;

(2) Weigh fermented *Cordyceps* Mycelia powder and *Schisandra chinens*, add ethanol, hot reflux, cool down, combine ethanol filtrate, filter, concentrate and dry the filtrate;

(3) Weigh pine pollen, digeratur in ethanol, combine the fluids and dry into dry extract;

(4) Take the above-mentioned three dry extracts, mix and pulverization, add starch, blend and prepare into compound preparation.

According to the pharmacodynamics study, this preparation has a new use of decreasing the cirrhotic portal hypertension. The study results were as follows:

I. Models and grouping: intraperitoneal injection of 0.5% dimethylnitrosamine (DMN) for successive 3 days followed by 4 days of rest, for a total of 4 weeks. After models were established, 2 rats were randomly selected and sacrificed to observe the pathologic change of livers. After hepatic cirrhosic was confirmed by pathological examination, animals were randomly divided into model group and the formula group. Animals in the formula group received intragastric administration of the formula strengthening body resistance and absorbing clots, while model group and normal group received same amount of drinking water, for 3 weeks.

II. Efficacy results:

1. Death and ascites in each group

Four weeks since modeling, no mammals died in each group. Mammals began to die in Week 5. By the end of Week 7, no mammals died in the normal group, 4 mammals died in the model group, 2 died in the formula group, and the cause of death was hepatic failure; ascites occurred most in the model group, and according to chi-square test, there was significant difference between the formula group and the model group. See Table 1 for details.

TABLE 1

Death and ascites in each group

| Group | n | Death (n) | Ascites (n) |
| --- | --- | --- | --- |
| Normal group | 14 | 0 | 0 |
| Model group | 13 | 4 | 6 |
| Formula group | 15 | 2 | 1* |

Note:
compared with model group
*p < 0.05

2. Comparison of liver body ratio and spleen body ratio in each group

Three weeks after model establishment (by the end of week 7), body weight (not including ascites) of the model group was significantly lower than that of the normal group. Liver/body ratio decreased to 0.029, and spleen/body ratio increased to 0.005. After treatment with the formula for 3 weeks, body weight of mammals was somewhat recovered. Compared with model group, liver/body ratio increased and spleen/body ratio decreased. See Table 2 for details.

TABLE 2

Comparison of liver/body ratio and spleen/body ratio in each group (means ± SD)

| Group | n | Body weight (g) | Liver/body | Spleen/body |
| --- | --- | --- | --- | --- |
| Normal group | 14 | 451 ± 40 | 0.032 ± 0.003 | 0.0026 ± 0.0003 |
| Model group | 9 | 343 ± 47## | 0.029 ± 0.005 | 0.0050 ± 0.0012## |
| Formula group | 13 | 363 ± 37 | 0.033 ± 0.002 | 0.0044 ± 0.001 |

Note:
compared with normal group,
P < 0.01

3. Pathological observation of hepatic tissue 3.1 HE staining observation of hepatic tissue Normal mammals have clear hepatic lobule structures. Hepatic cell cords are in radial arrangement around central veins, a few parasinoidal cells can be found, and thimbleful fibrous connective tissues were found in portal areas. 3 weeks after model establishment, there was massive hemorrhagic necrosis in livers of model group, and massive oncotic hepatic cells were found, meanwhile, there was massive inflammatory cell infiltration including lymphocytes and monocytes etc. Hepatic sinuses were distorted. Portal areas significantly broadened. Fibrous tissue under hyperplasia formed septa, which separated hepatic lobules into several pseudolobules of different sizes; in the formula group, there were different degrees of improvements in degeneration of hepatic cells, necrosis, intrahepatic hemorrhage and fibrous hyperplasia. See FIG. 1 for details.

4. Changes of portal venous pressure in each group

Figure 1:
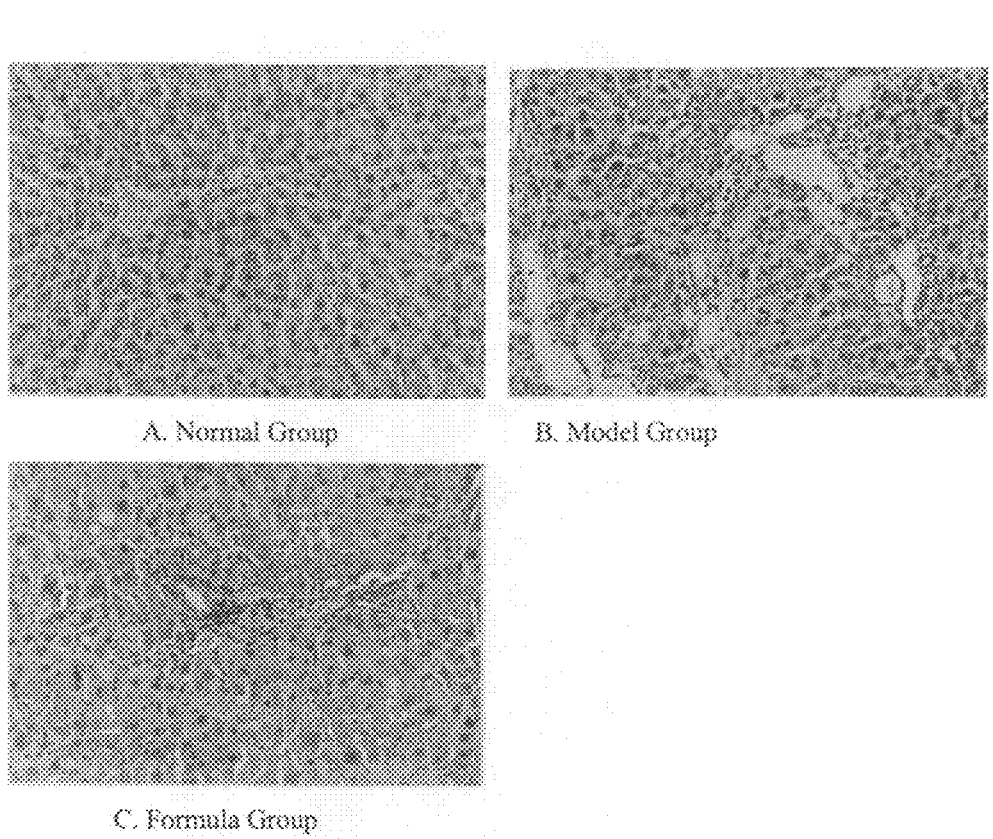
FIG. 1 Hepatic tissue inflammatory changes in DMN model mammals and the effect of the formula, hepatic tissue HE staining (×200).
Figure 2:
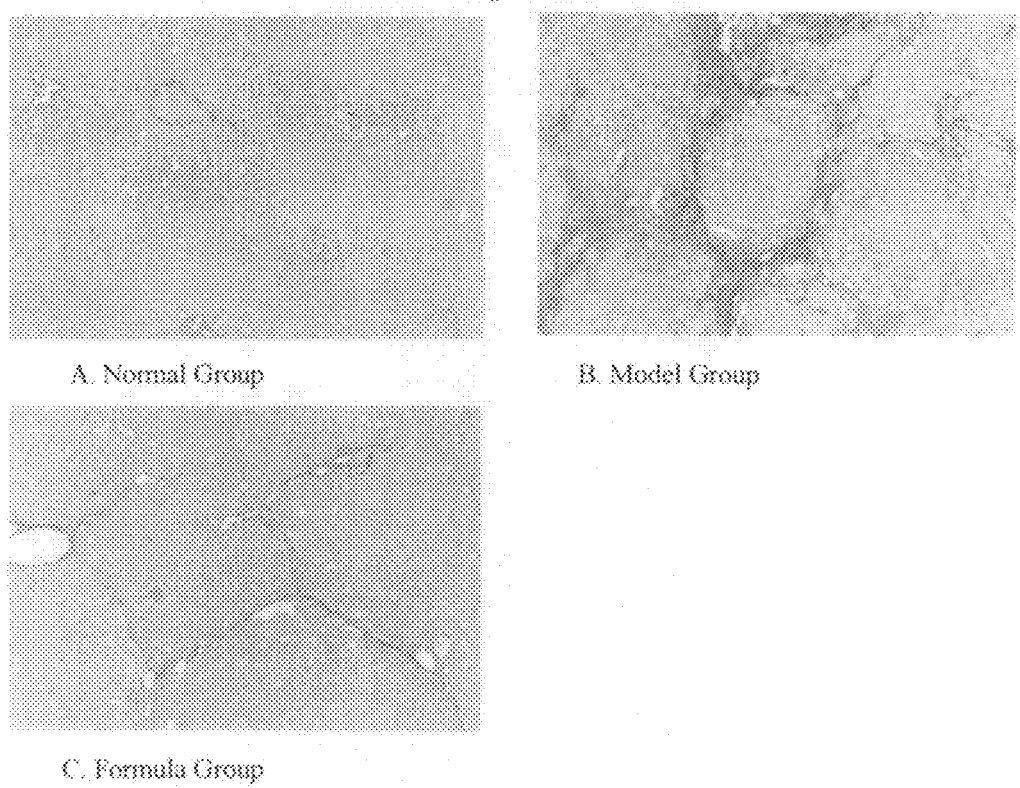
FIG. 2 Hepatic tissue collagen fiber deposition changes in DMN model mammals and the effect of the formula, hepatic tissue Sirius red staining (×200).
Figure 3:
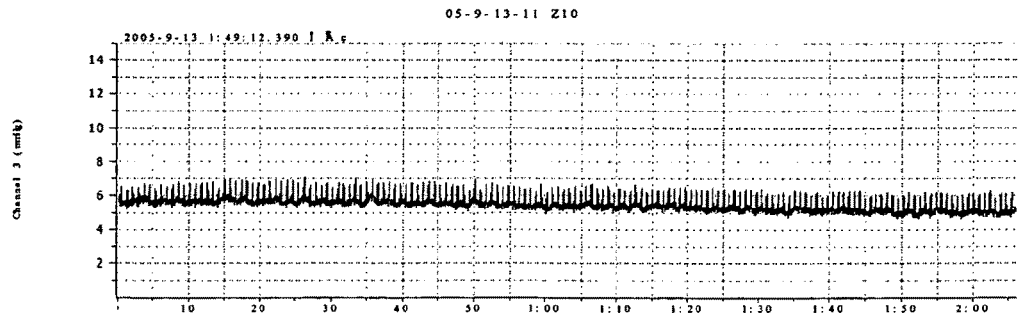
FIG. 3 Portal venous pressures of mammals in normal group.
Figure 4:
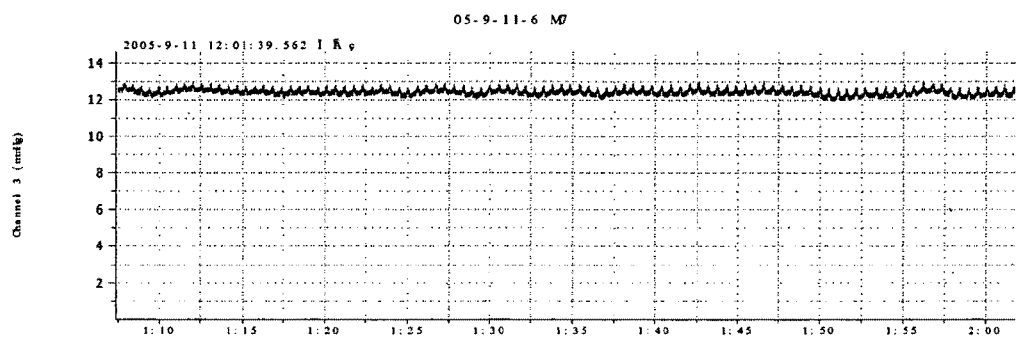
FIG. 4 Portal venous pressures of mammals in model group.
Figure 5:
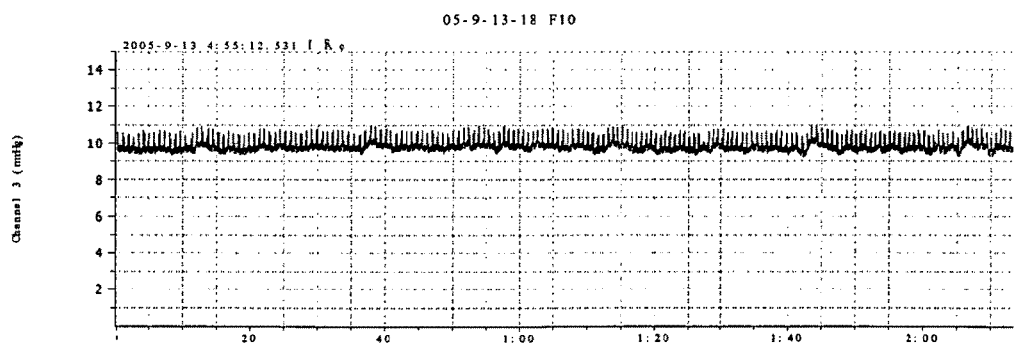
FIG. 5 Portal venous pressures of mammals in the formula group.

After DMN model establishment, portal venous pressure of the model group was significantly increased. Compared with the normal group, the increase reached 8 mmHg. After treatment with the formula for 3 weeks, portal venous pressure significantly decreased. Compared with the model group, there was significant difference between the two groups (p=0.035). See Table 7 and FIG. 3-5 for details.

TABLE 7

Changes of portal venous pressure in each group (means ± SD)

| Group | n | Portal venous pressure (mmHg) |
| --- | --- | --- |
| Normal group | 12 | 5.9 ± 1.0 |
| Model group | 9 | 13.9 ± 2.3## |
| Formula group | 13 | 9.3 ± 1.4* |

Note:
compared with normal group,
p < 0.01, compared with model group,
*p < 0.05

5. Changes of ET-1 content in hepatic tissue of mammals with hepatic cirrhosic

Three weeks after model establishment, ET-1 content in hepatic tissue of model group was significantly higher than the normal group, after treatment with the formula, ET-1 content in hepatic tissue decreased significantly, compared with concurrent model group, which had a statistical significance (p=0.044). See Table 8 for details.

TABLE 8

Changes of ET-1 content in hepatic tissue of mammals with hepatic cirrhosic (means ± SD)

| Group | n | ET-1 (pg/mg) |
|---|---|---|
| Normal group | 14 | 247.09 ± 49.51 |
| Model group | 9 | 344.48 ± 71.42## |
| Formula group | 13 | 292.13 ± 52.07* |

Note:
compared with normal group,
p < 0.01, compared with model group,
*p < 0.05

Figure 6:
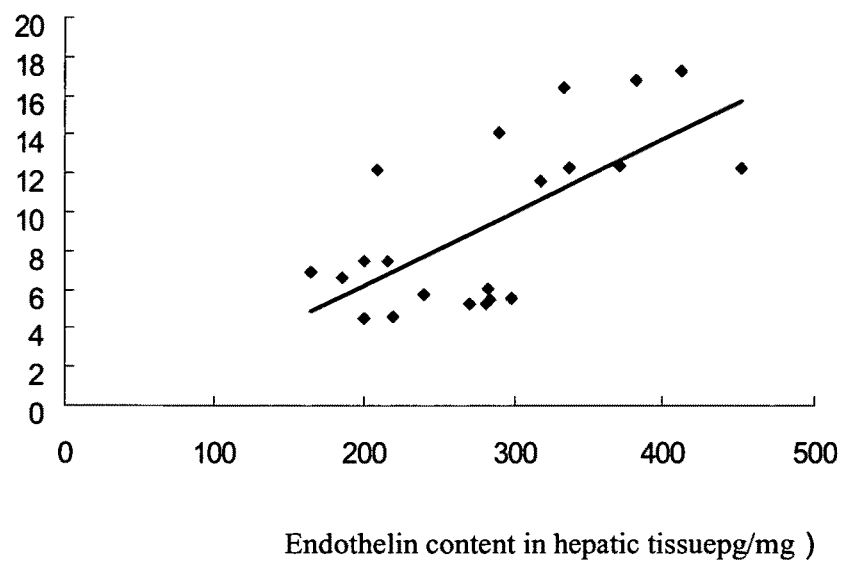
FIG. 6 Correlation between ET-1 content in hepatic tissue and portal venous pressure in mammals.

6. Correlation between ET-1 content in hepatic tissue and portal venous pressure in mammals There was significant positive correlation between ET-1 content in hepatic tissue and portal venous pressure in mammals with hepatic cirrhosic, r=0.675, p<0.01, see FIG. 6 for details.

Figure 7:
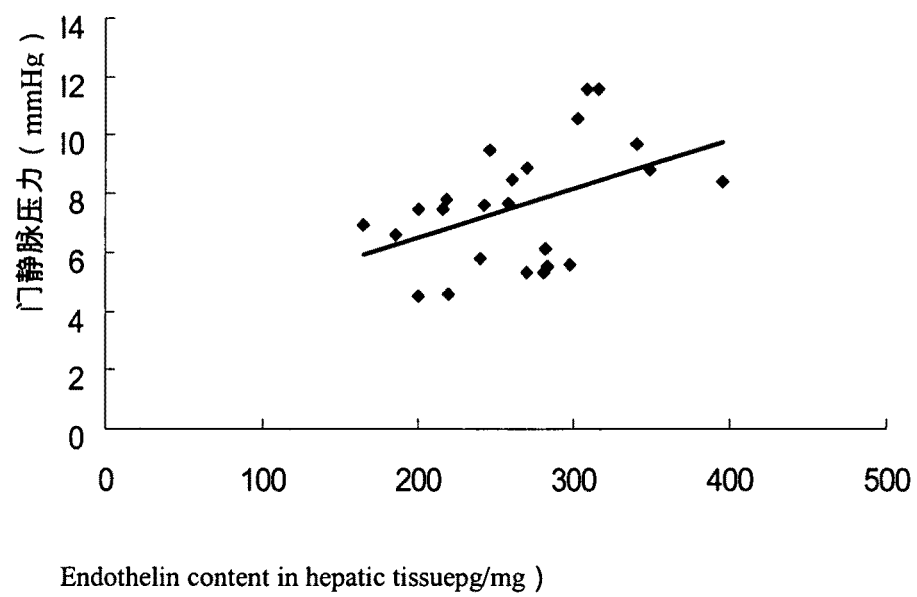
FIG. 7 Correlation between ET-1 content in hepatic tissue and portal venous pressure in mammals after treatment with the formula.

After treatment with the formula for 3 weeks, there was still a significant positive correlation between ET-1 content in hepatic tissue and portal venous pressure, r=0.447, p<0.05, see FIG. 7 for details.

III. Efficacy results analysis:

After 4 weeks, mammal model of hepatic cirrhosic was established. Animals were randomly grouping and treated with the formula for 3 weeks. The results indicated that after treatment with the formula, mortality and incidence of ascites significantly decreased as compared with model group. Liver body ratio increased, while spleen body ratio decreased; hepatic fibrosis was greatly alleviated, intrahepatic fibrous septa narrowed and shortened. Compared with the model group, portal venous pressure was significantly decreased by 4.6 mmHg, with the amplitude of 33%, the difference was quite remarkable.

In this study, ET-1 content in hepatic tissue of mammals in model group was significantly higher than normal group by about 40%, meanwhile, portal venous pressure of mammals in model group also significantly increased by 1.4 times, however, after treatment with the formula, portal venous pressure decreased and ET-1 content in hepatic tissue also decreased correspondingly. Correlation analysis indicated that there was a positive correlation between ET-1 content in hepatic tissue and portal venous pressure in mammals with hepatic cirrhosic, at the early stage of hepatic cirrhosic, the increase of intrahepatic resistance is the initial cause of portal hypertension, while HSC contraction enhancement is the most important cause of increased intrahepatic resistance. ET plays an important role in the initial causes of forming portal hypertension by promoting HSC contraction.

MODE OF CARRYING OUT THE INVENTION

Combining with the specific embodiments, further elaboration of this invention is given below. It should be understood that these embodiments are only for description of the present invention but not for the use of limiting the scope of the present invention. It should also be understood, after reading the contents taught in this invention, technicians in this field can make various changes or modification to this invention, these equivalent forms are all included in the scope defined by the claims attached to this application.

Case 1:

Wu$^{xx}$, male, 34 years, was diagnosed with "hepatic cirrhosic" in September 2002. He came to Shanghai 7$^{th}$ People's Hospital for further diagnosis and treatment. Examination of HBV-M revealed: "HBsAg (+), anti-HBe (+), anti-HBc (+)", HBV DNA (+), four items for serum hepatic fibrosis indicated: P-III-P (type III procollagen peptide) 1.81 ng/ml, IV-C (type IV collagen) 547 ng/ml, HA (hyaluronic acid) 377 ng/ml, LN (laminin) 369 ng/ml. Hepatic function was normal, Type B ultrasonography indicated optical thickening in liver, showing a chronic hepatopathy changes. Portal vein was 12 mm. The spleen was enlarged to 144 mm×52 mm. He was abdominal distension, anorexia, asthenia, and moderate gastric varices under gastroscope. Recovered after 1 month treatment with the capsules of strengthening body resistance and dissipating blood stasis, the four items for serum hepatic fibrosis were basically normal. In the re-examination half a year later, of the type B ultrasonography showed the portal vein was 11 mm, and the size of spleen decreased to 100 mm×39 mm. Patient continued treatment with the capsules, one year later, symptoms of abdominal distension, anorexia and asthenia etc. were alleviated. Gastroscopy performed in February 2003 showed mild gastric varices.

Case 2:

Chen $^{xx}$, male, 41 years, had chronic hepatitis B for 11 years. HBV-M examination in March 2003 indicated "HBsAg (+), anti-HBe (+), anti-HBc (+)". Hepatic function was normal. Type B ultrasonography showed the inside diameter of portal vein was 14 mm, portal vein flow rate was 15 mm/s, spleen size was 115 mm×37 mm. Gastroscopy showed moderate esophageal varices. Patient began to take capsules of strengthening body resistance and dissipating blood stasis.

One year later, re-examination indicated that the inside diameter of portal vein was 12 mm, portal vein flow rate was 19 mm/s, spleen size was 112 mm×35 mm and mild esophageal varices. After successive treatment for two years, examination in March 2005 showed the inside diameter of portal vein was 12 mm, portal vein flow rate was 21 mm/s, spleen size was 101 mm×31 mm, and esophageal varices disappeared.

The invention claimed is:

1. A method for treating a patient having hepatic cirrhosis comprising the steps of:
   administering an effective amount of a botanical pharmaceutical composition for strengthening body resistance and dissipating blood stasis to said patient for about one year to about two years, wherein said botanical pharmaceutical composition comprises 25-38% of *Salvia miltiorrhiza* extract, 20-25% of *Gynostemma pentaphyllum* extract, 1-6% of *Schisandra chinensis* alcohol extract, 19-26% of *Cordyceps* extract, 6-8% of pine pollen extract, and 6-10% of peach kernel extract, wherein the portal vein flow rate of said patient is increased by at least 27% after administration compared to the portal vein flow rate before administration of the botanical pharmaceutical composition.

2. The method in claim 1, further comprising the steps of:
   a. measuring the inside diameter of portal vein, and the size of the spleen in said patient prior to administration of said botanical pharmaceutical composition; and
   b. re-measuring the inside diameter of portal vein, and the size of the spleen in said patient after the administration of said botanical pharmaceutical composition, to determine the reduction of the portal venous pressure in said patient.

3. A method for reducing the portal venous pressure in a patient having hepatic cirrhosis, comprising the steps of:
   a. measuring the inside diameter of portal vein, the portal vein flow rate and the size of the spleen in said patient;
   b. administering an effective amount of a botanical pharmaceutical composition for strengthening body resistance and dissipating blood stasis to said patient for about one year to about two years, wherein said botanical pharmaceutical composition comprises 25-38% of *Salvia miltiorrhiza* extract, 20-25% of *Gynostemma pentaphyllum* extract, 1-6% of *Schisandra chinensis* alcohol extract, 19-26% of *Cordyceps* extract, 6-8% of pine pollen extract, and 6-10% of peach kernel extract; and
   c. re-measuring the inside diameter of portal vein, the portal vein flow rate and the size of the spleen in said patient, wherein the portal vein flow rate of said patient is increased by at least 27% compared to the portal vein flow rate of step a.

\* \* \* \* \*